(12) United States Patent
Song et al.

(10) Patent No.: US 10,674,247 B2
(45) Date of Patent: Jun. 2, 2020

(54) HEARING PROTECTION EARPHONE, HEARING PROTECTION METHOD AND COMPUTER PROGRAM STORAGE MEDIUM FOR THE SAME

(71) Applicant: MERRY ELECTRONICS (SUZHOU) CO., LTD., Suzhou, Jiangsu Province (CN)

(72) Inventors: Guoming Song, Suzhou (CN); Ming Zhu, Suzhou (CN); Feilong Cheng, Suzhou (CN); Chunyan Hu, Suzhou (CN); Jiawei Zhou, Suzhou (CN)

(73) Assignee: MERRY ELECTRONICS (SUZHOU) CO., LTD., Suzhou (CN)

( * ) Notice: Subject to any disclaimer, the term of this patent is extended or adjusted under 35 U.S.C. 154(b) by 0 days.

(21) Appl. No.: 16/416,616

(22) Filed: May 20, 2019

(65) Prior Publication Data
US 2019/0387304 A1   Dec. 19, 2019

(30) Foreign Application Priority Data
Jun. 19, 2018   (CN) .......................... 2018 1 0631569

(51) Int. Cl.
*H04R 1/10* (2006.01)
*G06F 3/16* (2006.01)
(Continued)

(52) U.S. Cl.
CPC ............ *H04R 1/1041* (2013.01); *A61B 5/117* (2013.01); *G06F 3/16* (2013.01); *G06F 3/165* (2013.01);
(Continued)

(58) Field of Classification Search
CPC .......... G06F 3/16; G06F 9/4451; G06F 3/005; G06F 3/165; G06K 9/00362;
(Continued)

(56) References Cited

U.S. PATENT DOCUMENTS

2006/0013079 A1* 1/2006 Rekimoto ............ H04R 1/1041
369/30.01
2009/0180639 A1* 7/2009 Dai ...................... A61B 5/6817
381/74
(Continued)

FOREIGN PATENT DOCUMENTS

CN          101222786 A      7/2008
CN          103399483 A     11/2013
(Continued)

*Primary Examiner* — Davetta W Goins
*Assistant Examiner* — Kuassi A Ganmavo
(74) *Attorney, Agent, or Firm* — Birch, Stewart, Kolasch & Birch, LLP (57) ABSTRACT

The present invention provides a hearing protection earphone, a hearing protection method and a computer program storage medium, comprising a sound control system including a wearing-status sensing module for monitoring a current wearing status of the hearing protection earphone, sending a first monitoring signal when it is determined that the hearing protection earphone is in a wearing state, and sending a second monitoring signal when it is determined that the hearing protection earphone is in a non-wearing state; and a main control module for enabling a play function corresponding to a play mode which is adapted to the hearing protection earphone currently when the first monitoring signal sent from the wearing-status sensing module is received, and counting a stand-by time of the protection earphone and turning off the hearing protection earphone after a preset stand-by time elapses when the second monitoring signal sent from the wearing-status sensing module is received.

21 Claims, 5 Drawing Sheets

(51) Int. Cl.
*G10L 17/00* (2013.01)
*G06K 9/00* (2006.01)
*G06F 9/445* (2018.01)
*A61B 5/117* (2016.01)

(52) U.S. Cl.
CPC ....... *G06F 9/4451* (2013.01); *G06K 9/00362* (2013.01); *G10L 17/005* (2013.01); *H04R 1/1083* (2013.01)

(58) Field of Classification Search
CPC .. G06K 9/00771; A61B 5/117; H04R 1/1041; H04R 1/1083; H04R 3/00; H04R 29/001; H04R 1/1058; G10L 17/005; H03G 3/20
See application file for complete search history.

(56) References Cited

U.S. PATENT DOCUMENTS

| | | | | |
|---|---|---|---|---|
| 2011/0299695 | A1* | 12/2011 | Nicholson | G10K 11/17833 381/71.6 |
| 2014/0037101 | A1* | 2/2014 | Murata | H04R 3/00 381/74 |
| 2014/0169579 | A1* | 6/2014 | Azmi | G10K 11/16 381/71.6 |
| 2014/0314247 | A1* | 10/2014 | Zhang | H04R 1/1041 381/74 |
| 2015/0119136 | A1* | 4/2015 | Kulavik | A63F 13/212 463/29 |
| 2015/0289055 | A1* | 10/2015 | Li | H04R 3/002 381/71.6 |
| 2015/0304761 | A1* | 10/2015 | Montazemi | H04R 1/1083 381/72 |
| 2017/0200442 | A1* | 7/2017 | Yamabe | G10K 11/178 |

FOREIGN PATENT DOCUMENTS

| | | | |
|---|---|---|---|
| CN | 104394491 A | * | 3/2015 |
| CN | 104581494 A | | 4/2015 |
| CN | 105704602 A | * | 6/2016 |
| CN | 104484150 B | | 8/2017 |
| CN | 107508979 A | | 12/2017 |
| JP | 2008289101 A | * | 11/2008 |
| WO | WO 2017/120960 A1 | | 7/2017 |

* cited by examiner

HEARING PROTECTION EARPHONE, HEARING PROTECTION METHOD AND COMPUTER PROGRAM STORAGE MEDIUM FOR THE SAME

CROSS-REFERENCE TO RELATED APPLICATIONS

This non-provisional application claims priority under 35 U.S.C. § 119(a) on Patent Application No. 201810631569.6 filed in P.R. China on Jun. 19, 2018, the entire contents of which are hereby incorporated by reference.

Some references, if any, which may include patents, patent applications and various publications, may be cited and discussed in the description of this invention. The citation and/or discussion of such references, if any, is provided merely to clarify the description of the present invention and is not an admission that any such reference is "prior art" to the invention described herein. All references listed, cited and/or discussed in this specification are incorporated herein by reference in their entireties and to the same extent as if each reference was individually incorporated by reference.

BACKGROUND OF THE INVENTION

1. Field of the Invention

The present invention relates to the technical field of audio devices, and especially relates to a hearing protection earphone, a hearing protection method and a computer program storage medium for the same.

2. Related Art

As for modern people, earphone and music have become daily necessities of people. Once wearing the earphone, people may enter into a sound field presented by the earphone without worrying about disturbing others. However, with development of industrial technologies, various noise sources produce various noisy sounds, such as, cars on the road, noise in the subway, and so on. In order to be capable of better hearing contents of music, most of time, we choose to increase the volume. However, hearing will be damaged if one person listens to music at a relatively high volume for a long time.

Further, under the industrial production environment, hearing and health of the workers may be damaged due to too much environmental noise. In particular, as for some specific industries, such as, steel and textile industry, working in noise for a long time or in noise at an excessive level will cause damage to hearing of human ears, even other diseases.

Medical research shows that listeners shall control the volume below 100 db when listening to music, and shall control the continuous listening time within one hour. Otherwise, it may cause permanent hearing damage. Meanwhile, there have been various patents of hearing protection applied to commercially available products or included in the related-art solutions from certain companies. However, these patents are mainly focused on protecting hearing by reducing the volume in accordance with music volume and working hours. Such manner is relatively simple, and does not consider different requirements of different users. For example, Chinese patent application No. CN201510041471.1 which is entitled "Hearing protection method and system and earphone based on earphone", proposes a method comprising steps of: transmitting information for enabling hearing protection mode to a control terminal when an earphone end receives the information for enabling hearing protection mode input by a user; setting a volume threshold, via the control terminal, according to the information for enabling hearing protection mode; judging whether a volume value corresponding to a volume regulation instruction is larger than the volume threshold when the control terminal receives the volume regulation instruction; if not, setting a current volume to be the volume value corresponding to the volume regulation instruction; or if yes, setting the current volume to be the volume threshold. This method defines a maximum volume of the earphone through the volume threshold, and releases a feeling of pressure to eardrums of human ears due to a sound pressure caused by the earphone, thereby achieving the hearing protection.

Accordingly, it is highly demanded to solve those inconveniences and deficiencies of the prior art in practical use.

SUMMARY OF THE PRESENT INVENTION

With respect to the above deficiencies, one object of the present invention is to provide a hearing protection earphone, a hearing protection method and a computer program storage medium for the same, which may be applicable to different users, and provide hearing protection adapted to different users.

In order to achieve the above object, the present invention provides a hearing protection earphone, comprising an earphone housing, a speaker disposed inside the earphone housing and a sound control system, the sound control system including: a wearing-status sensing module for monitoring a current wearing status of the hearing protection earphone, sending a first monitoring signal when it is determined that the hearing protection earphone is in a wearing state, and sending a second monitoring signal when it is determined that the hearing protection earphone is in a non-wearing state; and a main control module for enabling a play function corresponding to a play mode which is adapted to the hearing protection earphone currently when the first monitoring signal sent from the wearing-status sensing module is received, and counting a stand-by time of the protection earphone and turning off the hearing protection earphone after a preset stand-by time elapses when the second monitoring signal sent from the wearing-status sensing module is received.

In order to achieve another object of the present invention, the present invention further provides a hearing protection method using the above hearing protection earphone.

In order to achieve further object of the present invention, the present invention further provides a computer program storage medium for storing a computer program which is to be executable to implement the above hearing protection method.

The present invention provide a sound control system in a hearing protection earphone which includes a wearing-status sensing module for monitoring a current wearing status of the hearing protection earphone, and a main control module for enabling a play function corresponding to a play mode which is adapted to the hearing protection earphone currently according to the monitoring signal received from the wearing-status sensing module when the hearing protection earphone is in a wearing state, and counting a stand-by time of the protection earphone and turning off the hearing protection earphone after a preset stand-by time elapses when the hearing protection earphone is in a non-wearing state. With the hearing protection earphone having the above structure, the present invention may be applicable to different users and provide hearing protection adapted to different users. Moreover, the hearing protection earphone may automatically adjust the volume according to a length of wearing time, and automatically record the music play time of the user and gradually reduce the volume of music in the earphone after a period of time elapses according to a control algorithm based on parameters such as loudness of noise in the external environment, a denoising depth, thereby achieving the object of hearing protection without being perceived by the user. In addition, the main control module sends a denoiseing enable instruction signal when it is determined that the loudness of noise in the external environment reaches a preset noise threshold according to noise signals in the external environment of the earphone housing that are sampled by a sound sampling module. A denoising module executes a denoising operation on the audio presented by a speaker of the earphone when the denoiseing enable instruction signal is received. Accordingly, the denoising operation on the audio presented by the speaker of the earphone may be executed based on the parameters of noises in the environment of the earphone, thereby improving user's experience of listening to the audio presented by the earphone. Correspondingly, the hearing protection method and the computer program storage medium for the hearing protection earphone according to the present invention are capable of automatically adjusting the speaker volume of the earphone according to user's habits and preferences, and adjusting the volume according to the detected actually-wearing time, and thus may be applicable to different users and provide hearing protection adapted to different users.

DETAILED DESCRIPTION OF THE PRESENT INVENTION

To explain the objects, the technical solutions and the advantages of the present invention more definitely, the present invention will be described in detail with reference to the accompanying drawings and embodiments. It is to be understood that terms "one embodiment", "an embodiment" and "an exemplary embodiment" or the like used in the description indicate that the described embodiment may comprise specific features, structures or characteristics which are not necessarily included in each embodiment. Further, those terms does not necessarily refer to the same embodiment. Further, when specific features, structures or characteristics are described with reference to an embodiment, it is understood that those features, structures or characteristics may be incorporated into other embodiments, no matter whether it is definitely stated, which belongs to the knowledge range for the person skilled in the art, Although specific components or elements are indicated with some terms in the description and attached claims, it is understood by the ordinary persons in the art that technology users or manufacturers may use different names or terms to indicate the same component or element. The components or elements in the description and attached claims are not distinguished by different names, but by different functions of those components or elements. Terms "comprise" and "include" mentioned in the whole description and attached claims are open terminologies, and shall be interpreted as "include but not limited to". Further, term "connect" includes any direct or indirect electrical connection. Indirect electrical connection includes connection through other devices.

It is noted that in the description, terms such as "transverse", "longitudinal", "on", "below", "front", "back", "left", "right", "vertical", "horizontal", "top", "bottom", "ins", "out" indicate orientation or position relationship on the basis of the orientation or position relationship illustrated in the drawings, and are merely used to facilitate and simplifying the description of the present invention, instead of indicating or suggesting that the described device or element be necessarily arranged with such a specific orientation, or be necessarily constructed and operate in such a specific necessarily, which does not intend to limit the present invention.

Figure 1:
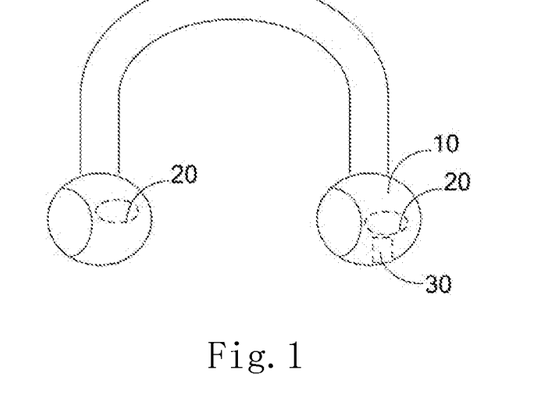
FIG. 1 is a diagram showing a structure of a hearing protection earphone according to an embodiment of the present invention.
Figure 2:
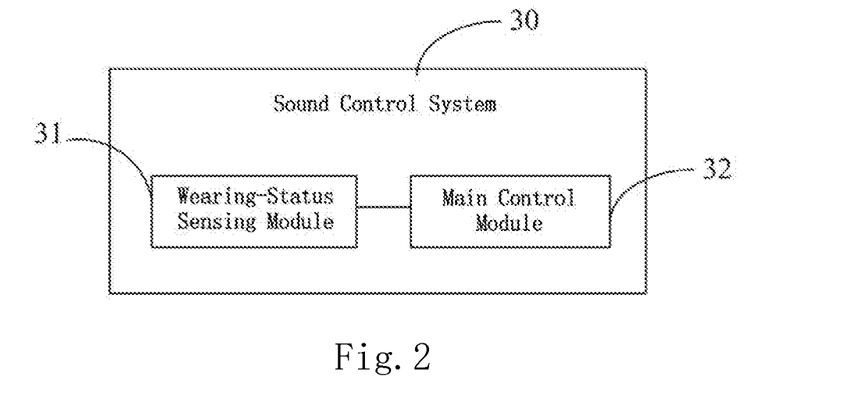
FIG. 2 is a schematic diagram showing a first part of a sound control system of the hearing protection earphone according to the embodiment of the present invention.

Referring to FIGS. 1 and 2, in an embodiment of the present invention, a hearing protection earphone 100 is provided, which comprises an earphone housing 10, a speaker 20 disposed inside the earphone housing 10 and a sound control system 30.

The sound control system 30 includes a wearing-status sensing module 31 and a main control module 32. The wearing-status sensing module 31 monitors a current wearing status of the hearing protection earphone 100, sends a first monitoring signal when it is determined that the hearing protection earphone 100 is in a wearing state, and sends a second monitoring signal when it is determined that the hearing protection earphone 100 is in a non-wearing state. The main control module 32 initiates a play function corresponding to a play mode which is adapted to the hearing protection earphone 100 currently when the first monitoring signal sent from the wearing-status sensing module 31 is received, and counting a stand-by time of the protection earphone 100 and turning off the hearing protection earphone 100 after a preset stand-by time elapses when the second monitoring signal sent from the wearing-status sensing module 31 is received In this embodiment, firstly, the wearing-status sensing module 31 monitors a current wearing status of the hearing protection earphone 100. When the hearing protection earphone 100 is in a wearing state, the main control module 32 initiates a play function corresponding to a play mode which is adapted to the hearing protection earphone 100 currently, so as to be adapted to different users. Different users have the same requirements for play parameters of an earphone. For example, as for elder people and children who require additional protection to hearing, their associated play parameters for presenting audio with an earphone, such as volume, listening time, need to satisfy certain medical requirements. On the other hand, some music fans have their personal preference, such as listening to music at a high volume for a long time. Therefore, the hearing protection earphone 100 may be adapted to different users in usage, and provide a corresponding play mode. Further, when the wearing-status sensing module 31 monitors that the hearing protection earphone 100 is in a non-wearing state, the main control module 32 will count the stand-by time of the protection earphone 100 and turn off the hearing protection earphone 100 after a preset stand-by time elapses, so as to save power.

Figure 3:
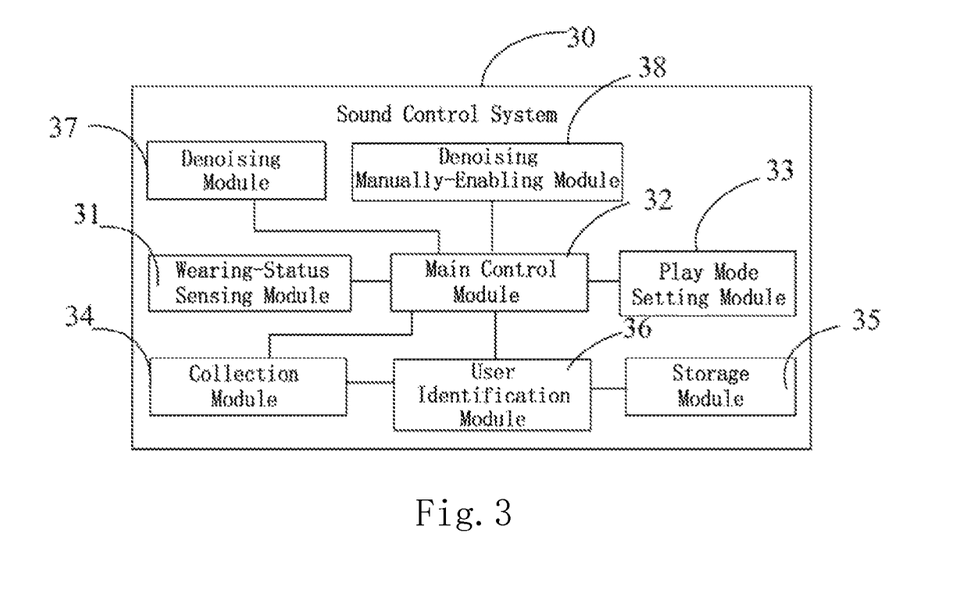
FIG. 3 is a schematic diagram showing a second part of the sound control system of the hearing protection earphone according to the embodiment of the present invention.

Referring to FIG. 3, in one embodiment of the present invention, the sound control system 30 further includes a play mode setting module 33, a collection module 34, a storage module 35, and a user identification module 36. The play mode setting module 33 may set the play mode to be a special group mode as a default, or set the play mode to be a self-adaptive mode upon receiving a mode switching instruction. The collection module 34 collects and sends user identity information. The storage module 35 stores user recognition information for verifying a user's identity, information about play functions corresponding to each play mode, and information about play volume of the hearing protection earphone associated with each user. The user identification module 36 matches the user identity information with the user recognition information in the storage module 35 in the self-adaptive mode, and sends successful-match information to the main control module 32 when the information are successfully matched such that the main control module 32 adjusts the play mode to a play mode matched with the user.

In this embodiment, as a default, the play mode of the hearing protection earphone 100 is set to be a special group mode through the play mode setting module 33. In the special group mode, play volume and/or play time of the hearing protection earphone 100 meet requirements for the elder people, children and hearing impaired people. Accordingly, once the user wears the hearing protection earphone 100 to listen to music, it is the special group mode in which the play volume or play time of audio may protect the user's hearing. Moreover, the play mode setting module 33 receives a mode switching instruction so that the play mode is set to be a self-adaptive mode. The self-adaptive mode may be adapted to user recognition information that have been stored in advance associated with different users and information about the play volume of the hearing protection earphone 100 associated with each user. Specifically, when the play mode is switched to the self-adaptive mode, the user identification module matches the user identity information collected by the collection module 34 with the user recognition information in the storage module 35, and if matched successfully, sends successful-match information to the main control module 32. According to the successful-match information, the main control module 32 switches the play mode to a play mode matched with the user. In this way, the hearing protection earphone 100 may be adapted to listening habits of different users using the hearing protection earphone 100. Preferably, the user identity information includes user voice information. The user may speak a predetermined phrase/sentence, for example, "I am Liming". Then, the main control module 32 may retrieve information about the play volume of the hearing protection earphone 100 associated with Liming that has been stored in the storage module 35, so as to adjust the volume of the speaker 20. Alternatively, in other embodiments, since voice of each people has his/her remarkable characteristics, the collection module 34 may collect audio of the user Liming's voice when Liming simply says a few words. Then, the user identification module 36 compares the audio with Liming's voice that has been stored in the storage module 35. If it is determined that they are the same person, the play mode may be switched to the play mode matched with Liming.

In one embodiment of the present invention, the play functions of the play mode includes: determining whether to enable a denoising function of the hearing protection earphone 100 according to loudness of noise in the current external environment of the hearing protection earphone 100. Since the hearing protection earphone 100 may initiate the denoising function automatically according to noise conditions in ambient environment, influence of the noise in ambient environment imposed on the audio presented by the speaker 20 is fully taken into consideration. Therefore, auditory perception of users may be improved.

No matter whether the denoising function is enabled or disabled, the hearing protection earphone 100 is turned off when the volume of audio from the hearing protection earphone 100 reaches a first volume threshold and/or the play time of the audio reaches a first time threshold, as the hearing protection function of the hearing protection earphone 100. For the purpose of hearing protection, mainly, play volume and play time of the audio heard by the user with the earphone are controlled. Therefore, thresholds are preset such that the hearing protection earphone 100 may be turned off, for example, when the play volume reaches a maximum volume 90 db or the play time reaches one hour, so as to protect the user's hearing from being damaged. The first volume threshold and the first time threshold may be different so as to match different use habits of different users.

Further, in the self-adaptive mode, the preset first volume threshold may be increased or decreased according to the stored information about the play volume of the hearing protection earphone 100 associated with the current user before the determination about whether the play volume of the audio reaches the preset first volume threshold, so as to be adapted to music fans who are used to listening music at a high volume, or some users who are used to listening at a low volume. For example, the first volume threshold may be 60 db, which is commonly used. However, when the first volume threshold reaches 60 db, in order to meet listening requirements of music fans who are used to listening at a high volume, the first volume threshold may be increased to 80 db, or a maximum volume threshold which the music fans are used to, such as, 100 db.

Referring to FIG. 3, in one embodiment of the present invention, the collection module 34 is a sound collection module 34. Additionally, the sound control system 30 further includes a denoising module 37. The sound collection module 34 collects noise signals in the external environment, and sends the noise signals to the main control module 32. The main control module 32 sends a denoising enable instruction signal to the denoising module 37 when the main control module 32 determines that the loudness of noise in the external environment reaches a preset noise threshold according to the noise signals. The denoising module 37 receives the denoising enable instruction signal, and executes a denoising operation on the audio from the speaker 20.

In this embodiment, considering that noise outside the hearing protection earphone 100 may also affect the quality of audio presented by the hearing protection earphone 100, which may bring the user with a poor auditory perception when the user listens to the audio presented by the hearing protection earphone 100. Therefore, parameter indexes about the noise in the external environment of the hearing protection earphone 100 are added in the denoising operation of the sound control system 30. Firstly, noise signals in the external environment of the earphone housing 10 are collected by the sound collection module 34. The main control module 32 determines whether it is necessary to send the denoising enable instruction signal to initiate the denoising module 37 according to the received noise signals and a preset noise threshold. When the denoising enable instruction signal is received, the denoising module 37 executes the denoising operation on the audio presented by the speaker 20. Accordingly, the denoising operation on the audio presented by the speaker 20 is executed according to parameters of noises in the external environment of the earphone housing 10. Since influence of the environmental noise is taken into consideration, auditory experience of the user who uses the hearing protection earphone 100 is improved.

Figure 4:
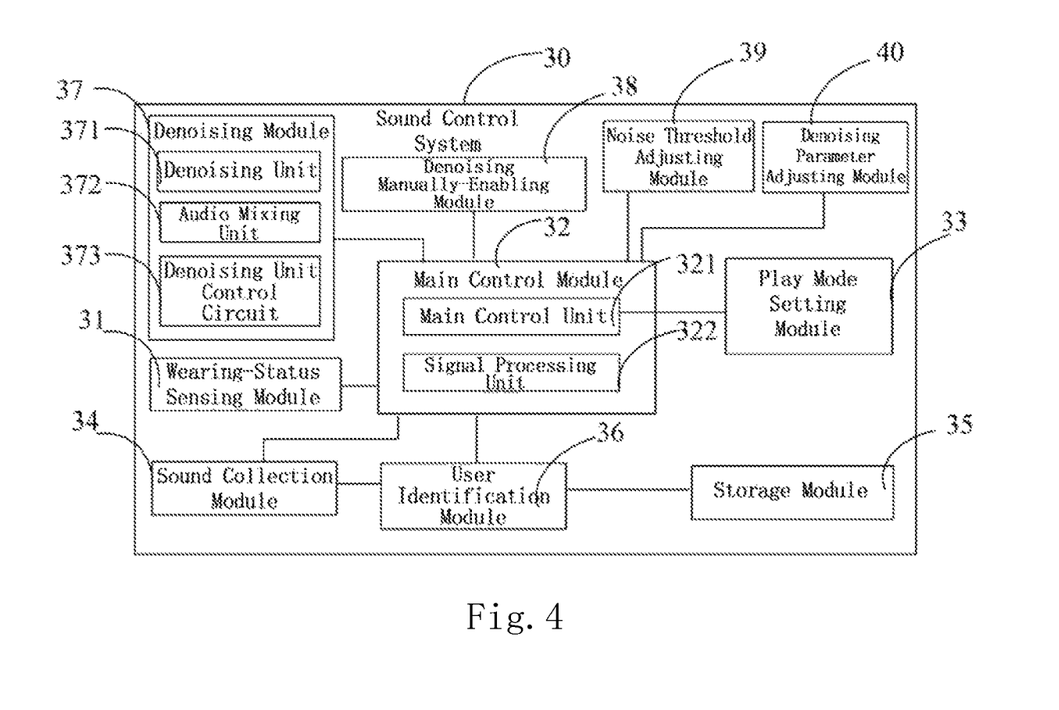
FIG. 4 is a schematic diagram showing a third part of the sound control system of the hearing protection earphone according to the embodiment of the present invention.

Referring to FIG. 4, in one embodiment of the present invention, the main control module 32 includes a main control unit 321 and a signal processing unit 322. The main control unit 321 performs digital-to-analogue conversion on the noise signals and the current audio signals from the speaker 20 and sends them to the signal processing unit 322, and controls the denoising module 37 to adjust denoising parameters. The signal processing unit 322 is connected to the main control unit 321 and the denoising module 37, respectively, and performs a signal amplification process on the noise signals and the audio signals that have been subjected to the digital-to-analogue conversion and sends them to the denoising module 37.

In this embodiment, the hearing protection earphone 100 may play audio in a wireless mode or a wired mode, such as, playing music using a Bluetooth earphone or a wired earphone. When playing music in the Bluetooth mode, the main control unit 321 receives Bluetooth music signals and converts them into analog signals through a DAC (digital-to-analog converter) within the main control unit 321, and then outputs them to the signal processing unit 322. The signal processing unit 322 performs a preliminary process on the analog audio signals, and then sends them to the denoising module 37. In an embodiment, the signal processing unit 322 includes a signal conversion and amplification circuit 3221. When the audio is presented in a wired mode upon powered on, the wired audio is directly sent to the denoising module 37 through an analog switch of the main control unit 321. In this way, denoised music may also be enjoyed in the wired mode.

In one embodiment of the present invention, preferably, the sound collection module 34 comprises a wired audio collection unit and a wireless audio collection unit. The wired audio collection unit collects a first noise signal in the external environment and sends the first noise signal to the main control module 32. The wireless audio collection unit collects a second noise signal in the external environment and sends the second noise signal to the main control module 32. The noise signals in the external environment may be respectively collected by the wired audio collection unit and the wireless audio collection unit, or collected by using both audio collection units simultaneously. The sound collection module 34 collects the noise signals through a wired microphone or a wireless microphone. When the main control unit 321 determines that the loudness of noise reaches a preset noise threshold according to the first noise signal, the main control unit 321 initiates the denoising module 37, performs digital-to-analogue conversion on the first noise signal and outputs it, sends the wired audio signal currently presented by the speaker 20 to the denoising module 37, and controls the denoising module 37 to adjust denoising parameters; and/or when the main control unit 321 determines that the loudness of noise in the external environment reaches a preset noise threshold according to the second noise signal, the main control unit 321 initiates the denoising module 37, performs digital-to-analogue conversion on the second noise signal and the wireless audio signal currently presented by the speaker 20 and outputs them, and controls the denoising module 37 to adjust denoising parameters. The signal processing unit 322 is connected to the main control unit 321 and the denoising module 37, respectively, and processes the received first noise signal and/or the second noise signal, and the wireless audio signals through the signal conversion and amplification circuit 3221 and then sends them to the denoising module 37, respectively.

In addition to the above automatic denoising function of the hearing protection earphone 100 described in the above embodiment, the hearing protection earphone 100 may also have a manual active denoising function.

Specifically, the sound control system 30 may further include a denoising manually-enabling module 38. The denoising manually-enabling module 38 is connected to the main control module 32, and receives a denoising function enable/disable operation instruction from the main control module 32 or sends it to the main control module 32. When the main control module 32 receives the denoising function enable/disable operation instruction, the main control module 32 sends an enable signal or a disable signal to the denoising module 37. The denoising manually-enabling module 38 is disposed on the housing 10, or disposed on a mobile communication terminal communicatively connected with the hearing protection earphone 100, so that the user can manually start a function switching module, and initiate the denoising function of the hearing protection earphone 100. Therefore, the main control unit 321 may enable/disable the denoising function of the hearing protection earphone 100 upon demand of the users in the wired audio play mode, so that the denoised audio may also be presented in the wired play mode. Further, the play mode setting module 33 may also be disposed on the housing 10, or disposed on a mobile communication terminal communicatively connected with the hearing protection earphone 100, and may be switched between a default play mode and a self-adaptive mode by pressing a corresponding key.

In one embodiment of the present invention, the denoising module 37 includes a denoising unit 371 and an audio mixing unit 372. The denoising unit 371 adjusts the denoising parameters under control of the main control unit 321, and performs a denoising operation on the noise signals and the audio signals sent from the signal processing unit 322. The audio mixing unit 372 mixes the noise signals with the audio signals that have been subjected to the denoising operation respectively, and outputs denoised audio.

In this embodiment, the denoising unit 371 performs the denoising operation on the noise signals according to the denoising parameters set by the main control unit 321. Then, the audio mixing unit 372 mixes the noise signals with the audio signals that have been subjected to the denoising operation respectively, and outputs the denoised audio. In this way, the noise in the audio outputted from the hearing protection earphone 100 may be reduced.

Further, as described in the above embodiment, if the sound collection module 34 collects the first noise signal and/or the second noise signal through the wired collection unit and the wireless collection unit, the denoising unit 371 performs the denoising operation on the first noise signal and/or the second noise signal according to the denoising parameters set by the main control unit 321. Then, the audio mixing unit 372 mixes the first and second noise signals with the wired audio signals or the wireless audio signals that have been subjected to the denoising operation respectively, and outputs the denoised audio. In this way, the noise in the audio outputted from the hearing protection earphone 100 may be reduced.

Here, the denoising parameters include a denoising depth, volume of the denoised audio and a adjustment time interval. The main control unit 321 controls the denoising module 37 to adjust the denoising depth to a corresponding preset range according to the loudness of noise in the environment.

When the main control unit 321 determines that the play time of the hearing protection earphone 100 reaches a second time threshold, the main control unit 321 sequentially reduces the volume of the denoised audio at the adjustment time interval according to the loudness of noise and the denoising depth. In this way, the volume may be reduced gradually, such that the user reduces the music volume he/she commonly used without being perceived by the user, thereby achieving the object of hearing protection without bringing any uncomfortable feelings.

Here, the second time threshold may be smaller than the first time threshold. For example, if the first time threshold is one hour, the second time threshold may be one half hour or fifty minutes. That is, the audio being played may be denoised before the audio is stopped. The main control unit 321 monitors the play time of the speaker 20, such that the volume may be automatically adjusted according to a length of time period during which the user wears the hearing protection earphone 100, so as to achieve the object of protecting the user's hearing. The main control unit 321 records the music play time of the user automatically. If the active denoising is preset, the music played in this time period is music that has been denoised actively. On the other hand, if the manually-enabling/disable denoising is preset, the denoising operation may be enabled/disabled on practical basis. After a period of time, the volume of music presented by the hearing protection earphone 100 may be reduced gradually, according to parameters such as the loudness of environmental noise and the denoising depth, under control of the main control unit 321, so as to achieve the object of protecting hearing without being perceived by the user. The hearing protection earphone 100 may automatically enable/disable an ANC (Active Noise Cancellation) function according to the loudness of noise in the external environment, and may adjust the denoising depth self-adaptively.

Specifically, the denoising parameters comprise the denoising depth, the volume of the denoised audio and the adjustment time interval. The main control unit 321 may controls the denoising module 37 to adjust the denoising depth to a corresponding preset range according to the loudness of noise.

When the main control unit 321 detects that the play time of the speaker 20 reaches the preset time threshold, the main control unit 321 sequentially reduces the volume of the denoised audio at the adjustment time interval according to the loudness of noise and the denoising depth. For example, if the loudness of the current environmental noise reaches 80 db, the noise seriously affects the user and prevents him from hearing the music played in the earphone. In such a case, denoising is required. In order to inhibit the noise from affecting the user listening to the music, it is required that the loudness of noise be decreased to be less than 50 db. Accordingly, the denoising depth is −30 db. As to the specific value of db, it may be set by the user as necessary, or alternatively set in combination with other specific denoising parameters. For example, a preset range of 50 db to 0 db may satisfy the requirements. Moreover, depending on different habits of different users for listening music, volume of denoised audio may be set differently. If a user is used to listening at a high volume, the volume may be set to be 60 db. If a user is used to listening at a low volume, the volume may be set to be 45 db or the like. To prevent the user from perceiving the denoising operation suddenly, the adjustment time interval may be set. For example, the loudness of noise may be reduced by 10 db every three minutes, and the volume of the denoised audio may be adjusted every five minutes by a differential amount of 5 db as compared with the volume of the last denoised audio. This allows the user to feel comfortable in auditory perception, rather than feeling a great and sudden change in auditory. Further, the time threshold may be set in a customary way. For example, when the volume of the denoised audio is 100 db, the time threshold is set to be one hour; and when the volume of the denoised audio is 70 db, the time threshold is set to be two hours. Alternatively, the time threshold may always be set to be one hour no matter what volume of the outputted denoised audio is.

In one embodiment of the present invention, the sound control system 30 further includes a noise threshold adjusting module 39 and a denoising parameter adjusting module 40. The noise threshold adjusting module 39 is connected to the main control unit 321, and is configured to set the noise threshold. The denoising parameter adjusting module 40 is also connected to the main control unit 321, and is configured to set the denoising parameters.

The noise threshold adjusting module 39 and the denoising parameter adjusting module 40 are disposed on a mobile communication terminal which is communicatively connected with the hearing protection earphone 100 in a wireless way. With the above two adjusting modules, the noise threshold and the denoising parameters may be adjusted according to user's requirements, respectively. For example, if the user is sensitive to the environmental noise, the noise threshold may be reduced, e.g., to be 50 db. Alternatively, if the user has different requirements for the time interval at which the volume of audio is reduced during the denoising process, he/she may set as desired. Preferably, the noise threshold adjusting module 39 and the denoising parameter adjusting module 40 are disposed on a mobile communication terminal which is communicatively connected with the hearing protection earphone 100 in a wireless way. For example, a relevant APP (Computer Application) may be installed on a mobile phone, to facilitate the adjustment of relevant parameters by the user so as to satisfy the requirements for the audio presented by the hearing protection earphone 100.

Further, the wearing-status sensing module 31 may be disposed on the earphone housing 10 at a position within or in proximal to a range corresponding to ear contours. The wearing-status sensing module 31 includes pressure sensors and optical sensors. By arranging the sensors on the earphone housing 10 at a position near the ear contours, a wearing status of the earphone housing 10 may be monitored accurately. With the wearing-status sensing module 31 including pressure sensors and optical sensors, when the user wears the earphone, it is certain that an external pressure will be received at the corresponding position on the earphone housing 10. By monitoring the generation or disappearance of the external pressure, whether the user is wearing the hearing protection earphone 100 may be detected. Alternatively, since light on the corresponding position of the earphone housing 10 becomes weak when the earphone is worn, whether the user is wearing the hearing protection earphone 100 may be detected by monitoring change of light intensity at the position.

Referring to FIG. 4, in one embodiment of the present invention, the denoising module 37 which integrates the denoising unit 371 and the audio mixing unit 372 may further include a denoising unit control circuit 373 connected to the denoising unit 371. Further, the user identification module 36 includes a voice waking-up and identification unit 361 connected to the main control unit 321.

Figure 5:
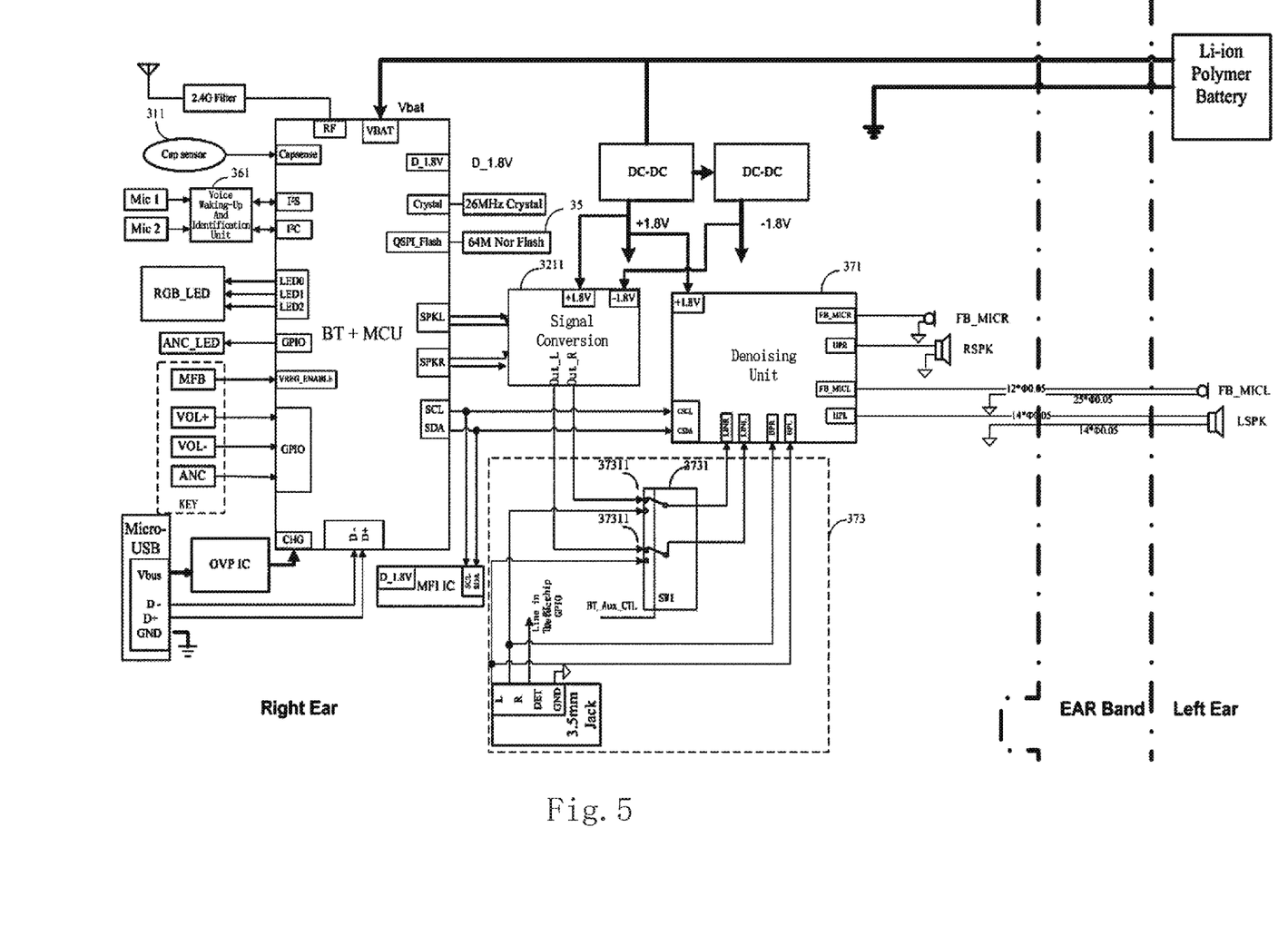
FIG. 5 is a diagram showing a circuit of the sound control system of the hearing protection earphone according to an embodiment of the present invention.

Referring to FIG. 5, the sound control system 30 particularly includes the following components.

The denoising unit 371 is provided with a CSCL interface, a CSDA interface, a LINR interface, a LINL interface, a BPR interface, a BPL interface and audio output left and right channels (FB_MICR, FB-MICL; LSPK, HPR). The denoising unit control circuit 373 includes a group of bipolar duplex switching circuits 3731. The bipolar duplex switching circuits 3731 includes two bipolar switches 37311 connected in parallel. One polar of an input terminal of one of the bipolar switches 37311 is connected to a right-channel signal output terminal (OUT_R) of the signal conversion and amplification circuit 3221. The same polar of the input terminal of the other one of the bipolar switches 37311 is connected to a left-channel signal output end (OUT L) of the signal conversion and amplification circuit 3221. Output terminals of those bipolar switches 37311 are respectively connected to the LINR interface and the LINL interface.

Further, the wearing-status sensing module 31 includes at least one sensor 311. The voice waking-up and identification unit 361 includes a DSP chip. The storage module 35 includes a 64M Nor Flash chip. The main control unit 321 includes a micro control unit (BT+MCU) 3211. The micro control unit (BT+MCU) 3211 is provided with a digital-to-analog converter, a bus extender (GPIO), wired audio interfaces (MIC_L, MIC_R), a wireless audio receiver (RF), an I'S interface, an I'C interface, an analog switch, a left-channel pin interface (SPKL), a right-channel pin interface (SPKR), a QSPI_Flash interface, a control line pin interface (SCL), and a data line pin interface (SDA). Here, a sensing signal receiver (Capsense) is connected to the at least one sensor 311. The DSP chip is connected to the I'S interface and the I'C interface. The QSPI_Flash interface is connected to the 64M Nor Flash chip. The wired audio interface (MIC_L, MIC_R) is connected to a wired microphone. The wireless audio receiver (RF) is connected to a wireless microphone. The left-channel pin interface (SPKL) and the right-channel pin interface (SPKR) are respectively connected to left-channel and right-channel signal input terminals of the signal conversion and amplification circuit 3221. The control line pin interface (SCL) and the data line pin interface (SDA) are respectively connected to the CSCL interface and the CSDA interface of the denoising module 371.

The denoising unit control circuit 373 further includes an earphone male connector (JACK). The earphone male connector has left-channel and right-channel output terminals (L, R) which are respectively connected to the other polar of the group of bipolar duplex switches 37311, the BPL interface and the BPR interface. Further, the denoising manually-enabling module 38 is connected to the bus extender (GPIO). In one embodiment, the denoising manually-enabling module 38 is implemented as an ANC key shown in FIG. 5. Although the denoising unit control circuit 373 includes a male connector (JACK) of the earphone as described above, it is not limited to a male connector, and may alternatively be implemented as a female connector. Alternatively, it may be implemented as a receptacle in the earphone body combined with an audio line, or otherwise may be implemented as a earphone body connected with an audio line which includes a plug.

In this embodiment, the wearing status of the earphone may be detected via wearing-status sensors, such as, pressure sensors or optical sensors. Pressure on a corresponding portion of the earphone housing 10 or change of the optical signals is detected by the sensors. Then, the change of the signals is sent to the micro control unit 3211 to detect the wearing status of the earphone. When the wearing-status sensors detect that the earphone is taken-off, the micro control unit 3211 may pause the music played by the speaker 20 and interrupt time-counting. When the wearing-status sensors detect that the earphone is worn again, the micro control unit 3211 continues the music played by the speaker 20 and continues the time-counting, so that an actual time period for listening to the music can be counted accurately. In this way, the hearing protection earphone may automatically adjust the volume or performs denoising operation on the played music according to a length of the actual time period for listening to the music. The denoising unit 371 collects environmental noise signals around the earphone housing 10 through the MIC (Microphone), and sends them to the micro control unit (MCU) 3211. The noise signals are subjected to a digital-to-analogue conversion process, and are then sent to the signal conversion and amplification circuit 3221 for a signal conversion and amplification processing through the left-channel pin interface (SPKL) and the right-channel pin interface (SPKR). Similarly, if a wireless audio signal is played currently, the wireless audio signal is also sent to the signal conversion and amplification circuit 3221 for the signal conversion and amplification processing. Subsequently, the signal conversion and amplification circuit 3221 sends the processed noise signals and the wireless audio signal to the denoising unit 371 through the CSCL interface and the CSDA interface. In the denoising unit 371, the processed noise signals are further processed and then mixed with the audio signal, and are outputted from the audio output left and right channels (FB_MICR, FB-MICL; LSPK, HPR), thereby achieving the active denoising function. The processing for a wired audio signal played currently differs from the processing for the wireless audio signal in that the wired audio signal is directly transmitted to the denoising unit 371 through the analog switch. The main control unit 321 may communicate with the denoising unit 371 through a communication bus, control the denoising unit 371 to set the denoising parameters, control to enable/disable the denoising function, adjust the denoising depth or the like. The denoising function may be enabled or disabled manually, or may be enabled or disabled automatically to implement an automatic enable/disable denoising function. When the automatic enable/disable denoising function is used, the MIC connected to the main control unit 321 collects external sound and sends it to the main control unit 321. The main control unit 321 determines whether the loudness of external noise reaches the preset noise threshold accordingly. The parameters of the noise threshold may be set through the APP in the mobile phone. When the preset threshold is reached, the main control MCU automatically enables the denoising function, and adjusts the denoising depth according to the loudness of external noise, so as to be adapted to different noise environments. Alternatively, those people who have special requirements may enable/disable the active denoising function manually through an ANC denoising switch.

Further, the voice waking-up and identification unit 361 may be implemented as a DSP (digital signal processor) chip. The MIC in a continuous working state may collect sound signals in ambient environment. When a matched sound is received, the sound control system 30 enters from a stand-by state to a working state, determines a corresponding earphone user according to the waking-up voice, and transmits the identity information to the main control unit (MCU) 321. In the hearing protection earphone 100, the sound control system 30 may also automatically adjust the volume according to the length of wearing time. The main control unit 321 may automatically count the time during which the user plays music, and after a period of time, gradually reduce volume of music presented by the earphone through a control algorithm in combination with parameters such as the loudness of environmental noise, the denoising depth and the like, thereby achieving the object of protecting hearing without being perceived by the user.

In one embodiment of the present invention, when the wearing-status sensing module 31 detects that the hearing protection earphone 100 is switched from a wearing state to a non-wearing states, the wearing-status sensing module 31 sends a third monitoring signal to the main control module 32. When the wearing-status sensing module 31 detects that the hearing protection earphone 100 is switched from a non-wearing state to a wearing states, the wearing-status sensing module 31 sends a fourth monitoring signal to the main control module 32. When the main control module 32 receives the third monitoring signal, the main control module 32 pauses the counting of the wearing time of the hearing protection earphone 100. When the main control module 32 receives the fourth monitoring signal, the main control module 32 resumes the counting of the wearing time of the hearing protection earphone 100, and sends a first control signal to the speaker 20. When the speaker 20 receives the first control signal, the speaker 20 stops the audio presented by the hearing protection earphone 100, or reduces the volume of the audio presented by the hearing protection earphone 100. Accordingly, the earphone wearing time of the user may be accurately counted. In other words, the time period during which the user wears the earphone to listen to the music may be accurately counted. Further, when the time reaches the preset first time threshold, such as one hour, a control signal may be sent to control the speaker 20, so as to control the speaker 20 to pause the audio, or to reduce the volume of the audio, thereby achieving hearing protection. Further, the present invention additionally includes wearing-status sensors for detecting the earphone wearing status. Accordingly, when the wearing-status sensors detect that the earphone is taken off, the music playing is paused and the time-counting is interrupted. When the wearing-status sensors detect that the earphone is worn again, the paused music is resumed and the time-counting is continued. In this way, the actual time period for listening to the music is accurately counted. Accordingly, continuity and completeness of listening to the audio can be ensured.

Figure 6:
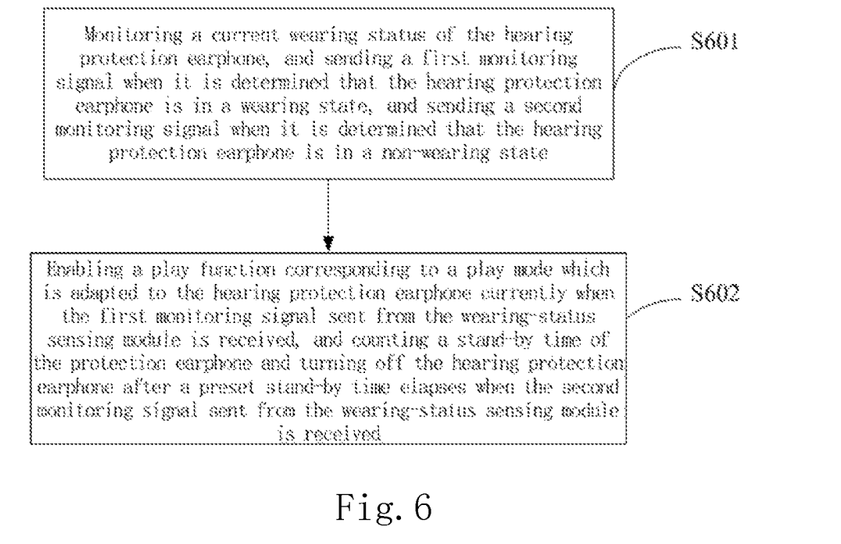
FIG. 6 is a flow diagram showing a first part of a hearing protection method according to an embodiment of the present invention.

Referring to FIG. 6, in order to achieve the object of the present invention, the present invention further provides a hearing protection method using the hearing protection earphone 100 according to any one of the above embodiments. The hearing protection method at least comprises the following steps.

In step S601, the wearing-status sensing module 31 monitors a current wearing status of the hearing protection earphone 100, sends a first monitoring signal when it is determined that the hearing protection earphone 100 is in a wearing state, and sends a second monitoring signal when it is determined that the hearing protection earphone 100 is in a non-wearing state.

In step S602, the main control module 32 enables a play function corresponding to a play mode which is adapted to the hearing protection earphone 100 currently when the first monitoring signal sent from the wearing-status sensing module 31 is received, and counts a stand-by time of the protection earphone 100 and turns off the hearing protection earphone 100 after a preset stand-by time elapses when the second monitoring signal sent from the wearing-status sensing module 31 is received.

In one embodiment of the present invention, before the step S601, the method further comprises the following step. The play mode setting module 33 sets the play mode to be a special group mode as a default, or set the play mode to a self-adaptive mode upon receiving a mode switching instruction.

The step S602 further includes the following steps. The collection module 34 collects and sends the user identity information. The user identification module 36 matches the user identity information with the user recognition information in the storage module 35 in the self-adaptive mode, and sends successful-match information to the main control module 32 after those information are successfully matched. The main control module 32 adjusts the play mode to a play mode matched with the user.

Here, the user identity information includes user voice information. The identification of a user may be performed based on the user voice information. The play function of the play mode includes: determining whether to enable the denoising function of the hearing protection earphone 100 according to the loudness of noise of the noise signals in the external environment of the earphone housing 10.

No matter whether the denoising function is enabled or disabled, the hearing protection earphone 100 is turned off when the volume of the audio presented by the hearing protection earphone 100 reaches a preset first volume threshold and/or the play time of the audio reaches a preset first time threshold, thereby achieving the hearing protection function of the hearing protection earphone 100;

In the self-adaptive mode, the preset first volume threshold may be increasing or decreased or decreased according to the stored volume information about the play volume of the hearing protection earphone associated with the current user before the determination about whether the play volume of the audio reaches the preset first volume threshold. In the special group mode, the play volume and/or the play time of the hearing protection earphone may be in conformity with medical requirements for elder people, children, and hearing impaired people.

In this embodiment, the special group mode is a play mode as default, in which the music volume is reduced according to the time period of listening to music in conformity with medical specifications and requirements strictly, thereby achieving the object of hearing protection. The self-adaptive mode may be enabled through a key combination. The hearing protection earphone 100 may be set according to an initial volume for listening to music by the user, detect a preferred volume for listening to music by the user, and reduce the music volume according to the time period for listening to music by the user, thereby achieving the object of hearing protection. When it is switched to the self-adaptive mode, the hearing protection earphone 100 may prompt the user to speak, collect and determine voices of respective users to identify the users so as to set different self-adaptive scales associative respective users. Further, the hearing protection earphone 100 determines automatically whether the active denoising function is enabled according to the loudness of noise in the ambient environment. The music listening time may be determined in combination with the results from the wearing-status sensors, so as to ensure that the music listening time of the user is effective, thereby preventing the sound control system 30 from making a wrong determination in a case where the user occasionally takes off the hearing protection earphone 100 to do something else.

The step of determining whether to enable the denoising function of the hearing protection earphone 100 according to the loudness of noise of the noise signals in external environment of the earphone housing 10 includes the following steps. The sound collection module collects the noise signals in the external environment, and sends the noise signals to the main control module 32. The main control module 32 sends a denoising enable instruction signal to the denoising module 37 when it is determined that the loudness of noise in the external environment reaches a preset noise threshold according to the noise signals. The main control module 32 monitors the volume of audio presented by the speaker 20, and sends the denoising enable instruction signal to the denoising module 37 when the detected volume reaches a preset volume threshold and/or the counted time reaches a second time threshold. The denoising module 37 receives the denoising enable instruction signal, and performs the denoising operation on the audio presented by the speaker 20.

Further, the hearing protection method further comprises a step of enabling the denoising function manually which includes the following steps. The denoising manually-enabling module 38 receives a denoising function enable/disable operation instruction from the main control module 32 or sends it to the main control module 32. After the main control module 32 receives the denoising function enable/disable operation instruction, the main control module 32 sends an enable signal or a disable signal to the denoising module 37.

When the denoising function is enabled, the denoising function includes the following steps. The main control unit 321 performs digital-to-analogue conversion on the noise signals and the current audio signals from the speaker 20 and sends them to the signal processing unit 322, and controls the denoising module 37 to adjust denoising parameters. The signal processing unit 322 performs a signal amplification process on the noise signals and the audio signals that have been subjected to the digital-to-analogue conversion, and sends them to the denoising module 37. The denoising unit 371 adjusts the denoising parameters under control of the main control unit 321, and performs the denoising operation on the noise signals and the audio signals sent from the signal processing unit 322. The audio mixing unit 372 mixes the noise signals with the audio signals that have been subjected to the denoising operation and outputs a denoised audio.

The denoising parameters include the denoising depth, the volume of the denoised audio and the adjustment time interval. The main control unit 321 controls the denoising module to adjust the denoising depth to a corresponding preset range according to the loudness of the environmental noise. When the main control unit 321 detects that the play time of the hearing protection earphone reaches a second time threshold, the main control unit 321 sequentially reduces the volume of the denoised audio at the adjustment time interval according to the loudness of noise and the denoising depth. Here, the second time threshold is smaller than the first time threshold.

In one embodiment of the present invention, after the step S602, the method further comprises the following step. When the wearing-status sensing module 31 detects that the hearing protection earphone 100 is switched from a wearing state to a non-wearing state, the wearing-status sensing module 31 sends a third monitoring signal to the main control module 32. When the wearing-status sensing module 31 detects that the hearing protection earphone 100 is switched from the non-wearing state to the wearing state, the wearing-status sensing module 31 sends a fourth monitoring signal to the main control module 32. When the main control module 32 receives the third monitoring signal, the main control module 32 pauses the counting of the wearing time of the hearing protection earphone 100. When the main control module 32 receives the fourth monitoring signal, the main control module 32 resumes the counting of the wearing time of the hearing protection earphone 100, and when the counted time reaches a preset first time threshold, sends a first control signal to the speaker 20. When the speaker 20 receives the first control signal, the speaker 20 stops the audio playing of the hearing protection earphone 100, or reduces the volume of the audio presented by the hearing protection earphone 100. Accordingly, the time period during which the user wears the earphone may be counted accurately, so as to protect the hearing of the user.

Figure 7:
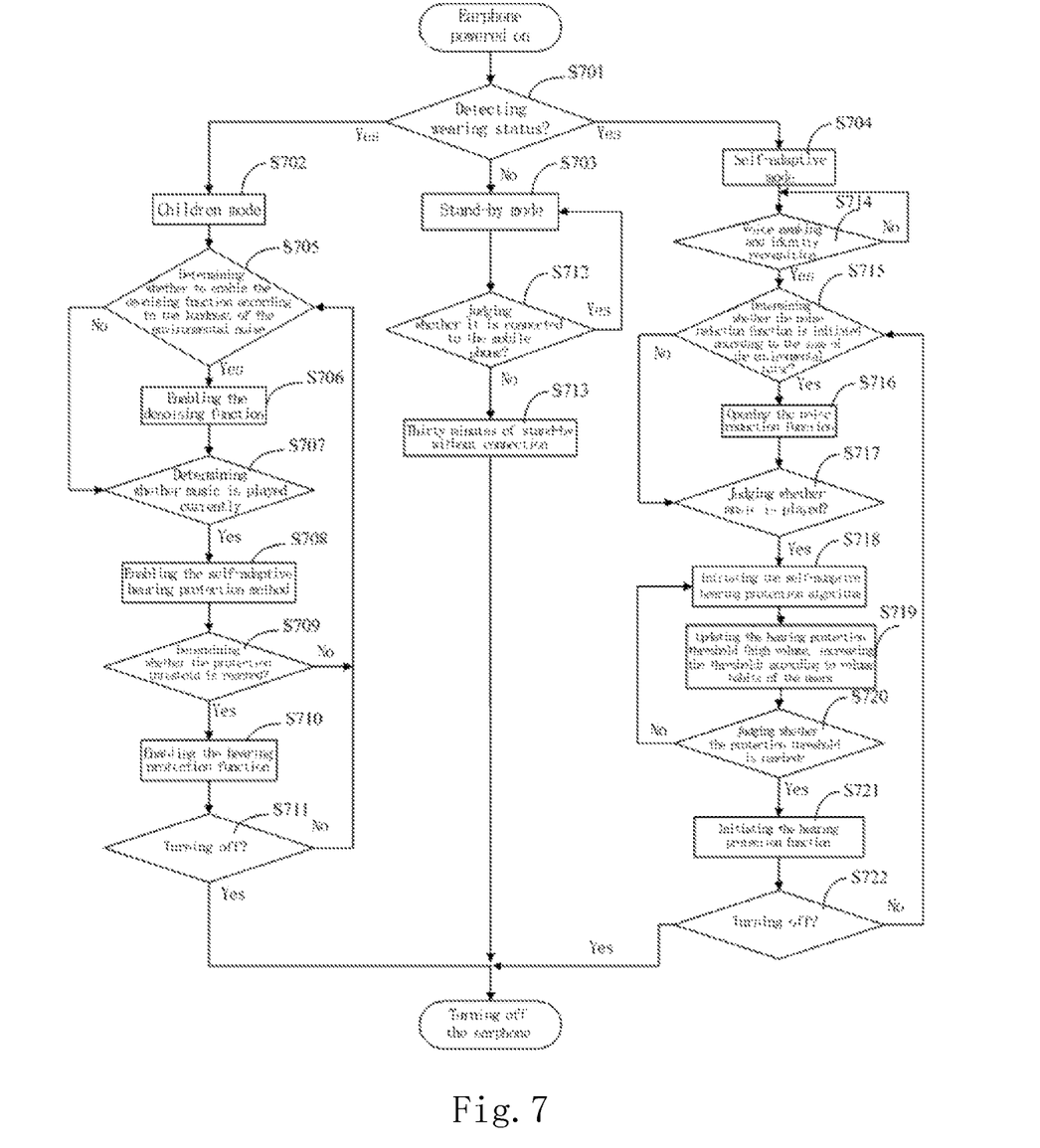
FIG. 7 is a schematic diagram showing a second part of the hearing protection method according to the embodiment of the present invention.

Referring to FIG. 7, in one embodiment of the present invention, a hearing protection method using the hearing protection earphone 100 is provided, which comprises the following steps:

S701: detecting whether the user wears the hearing protection earphone when the hearing protection earphone is powered-on, and if yes, proceeding to S702 or S704, or if not, proceeding to S703;

S702: switching to a children mode, i.e., a special group mode;

S703: switching to a stand-by mode;

S704: switching to a self-adaptive mode;

S705: determining whether to enable the denoising function according to the loudness of the environmental noise, and if yes, proceeding to S706, or if not, proceeding to S707;

S706: enabling the denoising function;

S707: determining whether music is played currently, and if yes, proceeding to S708, or if not, continuing to wait and if a time period during which music is not played reaches a preset time threshold, switching to the stand-by mode;

S708: enabling the self-adaptive hearing protection method;

S709: determining whether the protection threshold is reached, and if yes, enabling the hearing protection function, or if not, returning to S705;

S710: enabling the hearing protection function;

S711: determining whether to turn off, and if yes, turning off the hearing protection earphone 100, or if not, returning to S705;

S712: determining whether the mobile phone is connected, and if yes, returning to S703, or if not, proceeding to S713;

S713: turning off after twenty minutes in the stand-by mode without connection;

S714: determining whether the voice waking-up and identification are successful, and if yes, proceeding to S715, or if not, continuing to perform the voice waking-up and identification;

S715: determining whether to enable the denoising function according to the loudness of the environmental noise, and if yes, proceeding to S716, or if not, proceeding to S717;

S716: enabling the denoising function;

S717: determining whether to play music currently, and if yes, proceeding to S718, or if not, continuing to wait until the time period during which no music is played reaches a preset time threshold to indicate to switch to the stand-by mode;

S718: enabling the self-adaptive hearing protection method;

S719: increasing the hearing protection threshold for a user who is used to high volume according to the volume habits of the user;

S720: determining whether the protection threshold is reached, and if yes, proceeding to S721, or if not, returning to S719;

S721: enabling the hearing protection function;

S722: determining whether to turn off, and if yes, turning off the hearing protection earphone 100, or if not, returning to S715.

The hearing protection method in this embodiment is a hearing protection method integrated with wearing-status sensing as well as voice waking-up and identification. When the user uses the earphone, a conventional hearing protection earphone uses a hearing protection method according to music listening time and volume, and achieves the object of protecting hearing by reducing the volume or even turning off the earphone. However, in real life, many users are used to listening at a high volume. Therefore, if the conventional hearing protection earphone is used, auditory perception of some users could not be satisfied by directly reducing the volume, which may bring an annoying feeling to the user. The hearing protection method according to the present invention may wake up the earphone in the stand-by state with a voice recognition unit automatically, determine the corresponding earphone user quickly based on the collected voice information, retrieve the existing mode or previous use habits recorded automatically according to a self-adaptive algorithm, and increase one to two levels of volume appropriately on the basis of the hearing protection threshold according to the user habits, so as to satisfy the use habits of individual users. Further, in practice, the volume may be gradually decreased by adjusting a threshold for the hearing protection method of the earphone automatically, so that the user may reduce the commonly-used music volume unconsciously. In this way, the object of hearing protection may be achieved without annoying the user, so as to achieve an AI level of the hearing protection function.

Other specific steps and implementing devices of the hearing protection method according to the present invention have been described in detail in the embodiments of the hearing protection earphone 100 as described above, and are omitted here.

In order to achieve another object of the present invention, the present invention further provides a computer program storage medium for storing computer programs which may be executable to implement the hearing protection method described in the above embodiments. A part of the present invention may be applied to be a computer program product, such as, computer program instructions which may be executed by the computer to instruct the computer to invoke or provide the method and/or the technical solution of the present invention. The program instructions for invoking the method of the present invention may be stored in a fixed or removable recording medium, and/or sent over broadcasting or data flow in other signal carrying medium, and/or stored in a working memory of a computer device which is run according to the program instructions. Accordingly, one embodiment of the present invention comprises a device as shown in FIGS. 2-5, which includes a storage module 35 for storing the computer program instructions and a main control module 32 for executing the program instructions, wherein when the computer program instructions are executed by a processor, the device may be enabled to execute the method and/or the technical solution in the preceding embodiments.

It is noted that the present invention may be implemented in software and/or a combination of software and hardware. For example, it may be implemented with an application-specific integrated circuit (ASIC), a general-purpose computer or any other similar hardware devices. In one embodiment, the software program of the present invention may be executed by the processor to implement the above steps or functions. Similarly, the software program (including relevant data structures) of the present invention may be stored in a computer readable recording medium, such as, a RAM memory, a magnetic or optical driver, or a floppy disk, and the like. Further, some steps or functions of the present invention may be implemented in hardware, such as, circuits cooperated with the processor to execute various steps or functions.

To sum up, The present invention provide a sound control system in a hearing protection earphone which includes a wearing-status sensing module for monitoring a current wearing status of the hearing protection earphone, and a main control module for enabling a play function corresponding to a play mode which is adapted to the hearing protection earphone currently according to the monitoring signal received from the wearing-status sensing module when the hearing protection earphone is in a wearing state, counting a stand-by time of the protection earphone and turning off the hearing protection earphone after a preset stand-by time elapses when the hearing protection earphone is in a non-wearing state. With the hearing protection earphone having the above structure, the present invention may be applicable to different users and provide hearing protection adapted to different users. Moreover, the hearing protection earphone may automatically adjust the volume according to a length of wearing time, and automatically record the music play time of the user and gradually reduce the volume of music in the earphone after a period of time elapses according to a control algorithm based on parameters such as loudness of noise in the external environment, a denoising depth, thereby achieving the object of hearing protection without being perceived by the user. Further, the main control module sends a denoiseing enable instruction signal when it is determined that the loudness of noise in the external environment reaches a preset noise threshold according to noise signals in the external environment of the earphone housing that are sampled by a sound sampling module. A denoising module executes a denoising operation on the audio presented by a speaker of the earphone when the denoiseing enable instruction signal is received. Accordingly, the denoising operation on the audio presented by the speaker of the earphone may be executed based on the parameters of noises in the environment of the earphone, thereby improving user's experience of listening to the audio presented by the earphone. Correspondingly, the hearing protection method and the computer program storage medium for the hearing protection earphone according to the present invention are capable of automatically adjusting the speaker volume of the earphone according to user's habits and preferences, and adjusting the volume according to the detected actually-wearing time, and thus may be applicable to different users and provide hearing protection adapted to different users.

Of course, the present invention also may be implemented in many other embodiments, and the persons skilled in the art may make various modifications and variations according to the present invention without departing from the spirit and scope of the present invention. Those modifications and variations belong to the protection scope of the appended claims in the present invention.

What is claimed is:

1. A hearing protection earphone, comprising an earphone housing, a speaker disposed inside the earphone housing and a sound control system, the sound control system including:
   a wearing-status sensing module for monitoring a current wearing status of the hearing protection earphone, sending a first monitoring signal when it is determined that the hearing protection earphone is in a wearing state, and sending a second monitoring signal when it is determined that the hearing protection earphone is in a non-wearing state; and
   a main control module for enabling a play function corresponding to a play mode which is adapted to the hearing protection earphone currently when the first monitoring signal sent from the wearing-status sensing module is received, and counting a stand-by time of the protection earphone and turning off the hearing protection earphone after a preset stand-by time elapses when the second monitoring signal sent from the wearing-status sensing module is received;
   wherein the play functions of the play mode includes:
      determining whether to enable a denoising function of the hearing protection earphone according to loudness of noise of noise signals in the external environment of the earphone housing;
      turning off the hearing protection earphone when the play volume of audio from the hearing protection earphone reaches a first volume threshold and/or the play time of the audio reaches a first time threshold, no matter whether the denoising function s enabled or disabled; and
      increasing or decreasing the preset first volume threshold according to the stored information about the play volume of the hearing protection earphone associated with the current user before the determination about whether the play volume of the audio reaches the preset first volume threshold, in the self-adaptive mode.

2. The hearing protection earphone according to claim 1, wherein the sound control system further includes:
   a play mode setting module for setting the play mode to be a special group mode as a default, or setting the play mode to a self-adaptive mode upon receiving a mode switching instruction;
   a collection module for collecting and sending user identity information;
   a storage module for storing user recognition information for verifying a user's identity, information about play functions corresponding to each play mode, and information about play volume of the hearing protection earphone associated with each user;
   a user identification module for matching the user identity information with the user recognition information in the storage module in the self-adaptive mode, and sending successful-match information to the main control module when the information are successfully matched such that the main control module adjusts the play mode to a play mode matched with the user.

3. The hearing protection earphone according to claim 2, wherein the user identity information includes user voice information; and
   wherein, in the special group mode, the play volume and/or the play time of the hearing protection earphone are in conformity with medical requirements for elder people, children, and hearing impaired people.

4. The hearing protection earphone according to claim 3, wherein the collection module is a sound collection module, and the sound control system further includes a denoising module, and
   wherein the sound collection module collects noise signals in the external environment, and sends the noise signals to the main control module;
   the main control module sends a denoising enable instruction signal to the denoising module when the main control module determines that the loudness of noise in the external environment reaches a preset noise threshold according to the noise signals;
   the denoising module receives the denoising enable instruction signal, and executes a denoising operation on the audio from the speaker.

5. The hearing protection earphone according to claim 4, wherein the main control module includes:
   a main control unit for performing digital-to-analogue conversion on the noise signals and the current audio signals from the speaker, and sending them to a signal processing unit, and controlling the denoising module to adjust denoising parameters; and
   the signal processing unit connected to the main control unit and the denoising module, respectively, for performing a signal amplification process on the noise signals and the audio signals that have been subjected to the digital-to-analogue conversion and sending them to the denoising module.

6. The hearing protection earphone according to claim 5, wherein the sound control system further includes:
   a denoising manually-enabling module connected to the main control module, for receiving a denoising function enable/disable operation instruction from the main control module or sending it to the main control module,
   wherein when the main control module receives the denoising function enable/disable operation instruction, the main control module sends an enable signal or a disable signal to the denoising module.

7. The hearing protection earphone according to claim 5, wherein the denoising module includes:
   a denoising unit for adjusting the denoising parameters under control of the main control unit, and performing a denoising operation on the noise signals and the audio signals sent from the signal processing unit; and
   an audio mixing unit for mixing the noise signals with the audio signals that have been subjected to the denoising operatic and outputting denoised audio.

8. The hearing protection earphone according to claim 7, wherein the denoising parameters include a denoising depth, volume of the denoised audio and an adjustment time interval,
   wherein, the main control unit controls the denoising module to adjust the denoising depth to a corresponding preset range according to the loudness of noise in the environment, and
   when the main control unit determines that the play time of the hearing protection earphone reaches a second time threshold, the main control unit sequentially reduces the volume of the denoised audio at the adjustment time interval according to the loudness of noise and the denoising depth, and wherein the second time threshold is less than the first time threshold.

9. The hearing protection earphone according to claim 7, wherein the sound control system further includes:
a noise threshold adjusting module connected to the main control unit and configured to set the noise threshold; and
a denoising parameter adjusting module connected to the main control unit and configured to set the denoising parameters.

10. The hearing protection earphone according to claim 9, wherein the noise threshold adjusting module and the denoising parameter adjusting module are disposed on a mobile communication terminal communicatively connected with the earphone in a wireless manner.

11. The hearing protection earphone according to claim 7, wherein the denoising module integrated with the denoising unit and the audio mixing unit further includes a denoising unit control circuit connected to the denoising unit, and
the user identification module includes a voice waking-up and identification unit connected to the main control unit.

12. The hearing protection earphone according to claim 11, wherein the denoising unit is provided with a CSCL interface, a CSDA interface, a LINR interface, a LINT interface, a BPR interface, a BPL interface, and audio output left and right channels,
wherein the denoising unit control circuit includes a group of bipolar duplex switching circuits which includes two bipolar switches connected in parallel, one polar of an input terminal of one of the bipolar switches being connected to a right-channel signal output terminal of a signal conversion and amplification circuit, the same polar of the input terminal of the other one of the bipolar switches being connected to a left-channel signal output end of the signal conversion and amplification circuit, and output terminals of the bipolar switches are respectively connected to the LINK interface and the LINL interface.

13. The hearing protection earphone according to claim 11, wherein the wearing-status sensing module includes at least one sensor;
the storage module includes a memory chip;
the voice waking-up and identification unit includes a DSP chip; and
the main control unit includes a micro control unit, which is provided with a digital-to-analog converter, a bus extender, a sensing signal receiver, wired audio interfaces, a wireless audio receiver, an I'S interface, an I'C interface, an analog switch, a left-channel pin interface, a right-channel pin interface, a QSPI_Flash interface, a control line pin interface, and a data line pin interface, and
wherein the sensing signal receiver is connected to the at least one sensor;
the DSP chip is connected to the I'S interface and the I'C interface;
the QSPI_Flash interface is connected to the memory chip;
the wired audio interface is connected to a wired microphone;
the wireless audio receiver is connected to a wireless microphone;
the left-channel pin interface and the tight-channel pin interface are respectively connected to left-channel and right-channel signal input terminals of the signal conversion and amplification circuit; and
the control line pin interface and the data line pin interface are respectively connected to the CSCL interface and the CSDA interface of the denoising module.

14. The hearing protection earphone according to claim 13, wherein the denoising unit control circuit further includes an earphone receptacle having left-channel and right-channel signal output terminals connected to the other polar of the group of bipolar duplex switches, the BPL interface and the BPR interface.

15. The hearing protection earphone according to claim 14, wherein the denoising manually-enabling module is disposed on the housing, or is disposed on a mobile communication terminal communicatively connected with the hearing protection earphone and is connected with the bus extender.

16. The hearing protection earphone according to claim 4, wherein the sound collection module collects through a wired microphone or a wireless microphone.

17. The hearing protection earphone according to claim 4, wherein the main control module monitors the play volume from the speaker, and sends the denoising enable instruction signal to the denoising module when the detected volume reaches a preset volume threshold and/or the counted time reaches a second time threshold.

18. The hearing protection earphone according to claim 1, wherein the wearing-status sensing module is disposed on the earphone housing at a position within or in proximal to a range corresponding to ear contours, and
the wearing-status sensing module includes pressure sensors and optical sensors.

19. The hearing protection earphone according to claim 1, wherein
when the wearing-status sensing module detects that the h protection earphone is switched from a wearing state to a non-wearing state, the wearing-status sensing module sends a third monitoring signal to the main control module,
when the wearing-status sensing module detects that the hearing protection earphone is switched from the non-wearing state to the wearing state, the wearing-status sensing module sends a fourth monitoring signal to the main control module,
when the main control module receives the third monitoring signal, the main control module pauses the counting of the wearing time of the hearing protection earphone,
when the main control module receives the fourth monitoring signal, the main control module resumes the counting of the wearing time of the hearing protection earphone, and when the counted time reaches a preset first time threshold, sends a first control signal to the speaker, and
when the speaker receives the first control signal, the speaker stops the audio playing of the hearing protection earphone, or reduces the play volume of the audio from the hearing protection earphone.

20. A hearing protection method using a hearing protection earphone according to claim 1, comprising:
a wearing-status sensing step for monitoring a current wearing status of the hearing protection earphone, sending a first monitoring signal when it is determined that the hearing protection earphone is in a wearing state, and sending a second monitoring signal when it is determined that the hearing protection earphone is in a non-wearing state; and a main control step for enabling a play function corresponding to a play mode which is adapted to the hearing protection earphone currently when the first monitoring signal is received, and counting a stand-by time of the protection earphone and turning off the hearing protection earphone after a preset stand-by time elapses when the second monitoring signal is received;

wherein the play functions of the play mode includes:

determining whether to enable a denoising function of the hearing protection earphone according to loudness of noise of noise signals in the external environment of the earphone housing;

turning off the hearing protection earphone when the play volume of audio from the hearing protection earphone reaches a first volume threshold and/or the play time of the audio reaches a first time threshold, no matter whether the denoising function is enabled or disabled; and increasing or decreasing the preset first volume threshold according to the stored information about the play volume of the hearing protection earphone associated with the current user before the determination about whether the play volume of the audio reaches the preset first volume threshold, in the self-adaptive mode.

21. A non-transitory computer program storage medium for storing a computer program, wherein when executed by a processor, the program implements a hearing protection method, wherein the method comprises:

a wearing-status sensing step for monitoring a current wearing status of the hearing protection earphone, sending a first monitoring signal when it is determined that the hearing protection earphone is in a wearing state, and sending a second monitoring signal when it is determined that the hearing protection earphone is in a non-wearing state, and a main control step for enabling a play function corresponding to a play mode which is adapted to the hearing protection earphone currently when the first monitoring signal is received, and counting a stand-by time of the protection earphone and turning off the hearing protection earphone after a preset stand-by time elapses when the second monitoring signal is received;

wherein the play functions of the play mode includes:

determining whether to enable a denoising function of the hearing protection earphone according to loudness of noise of noise signals in the external environment of the earphone housing;

turning off the hearing protection earphone when the play volume of audio from the hearing protection earphone reaches a first volume threshold and/or the play time of the audio reaches a first time threshold, no matter whether the denoising function is enabled or disabled; and increasing or decreasing the preset first volume threshold according to the stored information about the play volume of the hearing protection earphone associated with the current user before the determination about whether the play volume of the audio reaches the preset first volume threshold, in the self-adaptive mode.

* * * * *